(12) United States Patent
Orban, III

(10) Patent No.: US 9,364,201 B2
(45) Date of Patent: Jun. 14, 2016

(54) MINIMALLY INVASIVE REMOVAL DEVICE WITH BREAKAWAY SHEATH

(75) Inventor: Joseph P. Orban, III, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 972 days.

(21) Appl. No.: 13/226,556

(22) Filed: Sep. 7, 2011

(65) Prior Publication Data

US 2011/0319788 A1  Dec. 29, 2011

Related U.S. Application Data

(63) Continuation of application No. 10/508,445, filed as application No. PCT/US03/09133 on Mar. 21, 2003, now Pat. No. 8,016,771.

(60) Provisional application No. 60/368,191, filed on Mar. 27, 2002.

(51) Int. Cl.
*A61B 5/00* (2006.01)
*A61B 17/00* (2006.01)

(52) U.S. Cl.
CPC . *A61B 17/00234* (2013.01); *A61B 2017/00287* (2013.01)

(58) Field of Classification Search
CPC .. A61B 10/02; A61B 17/22; A61B 10/00234; A61B 2017/00287; A61J 1/12
USPC ........ 600/562; 606/127, 128, 1, 114; 604/349
See application file for complete search history.

(56) References Cited

U.S. PATENT DOCUMENTS

| | | | |
|---|---|---|---|
| 30,471 | A | 10/1860 | Dudley |
| 156,477 | A | 11/1874 | Bradford |
| 1,609,014 | A | 11/1926 | Dowd |
| 3,800,781 | A | 4/1974 | Zalucki |
| 4,557,255 | A | 12/1985 | Goodman |
| 4,744,363 | A | 5/1988 | Hasson |
| 4,790,812 | A | 12/1988 | Hawkins, Jr. et al. |
| 4,886,509 | A | 12/1989 | Mattsson |
| 4,927,427 | A | 5/1990 | Kriauciunas et al. |
| 4,997,435 | A | 3/1991 | Demeter |
| 5,037,379 | A | 8/1991 | Clayman et al. |
| 5,074,867 | A | 12/1991 | Wilk |
| 5,084,054 | A | 1/1992 | Bencini et al. |
| 5,143,082 | A | 9/1992 | Kindberg et al. |
| 5,147,371 | A | 9/1992 | Washington et al. |

(Continued)

FOREIGN PATENT DOCUMENTS

| DE | 25796 | 8/1883 |
|---|---|---|
| DE | 8435489 | 12/1984 |

(Continued)

*Primary Examiner* — Max Hindenburg

(57) ABSTRACT

A tissue removal device is disclosed which includes an elongate shaft having a distal end and a proximal end, wherein the elongate shaft defines a longitudinal axis, a bag support defining an opening, the bag support being collapsible and expandable to open and close the opening, a bag operatively attached to the bag support, the bag having an open first end operatively secured to the bag support and a closed end, the first end being connected to the support so that when the bag support is in the collapsed position the bag opening is substantially closed, the bag having folds including at least one transverse fold. The tissue removal device may further include a tube for receiving the shaft, bag support and bag.

18 Claims, 3 Drawing Sheets

(56) References Cited

U.S. PATENT DOCUMENTS

| | | |
|---|---|---|
| 5,149,159 A | 9/1992 | Bardes |
| 5,176,687 A | 1/1993 | Hasson et al. |
| 5,190,542 A | 3/1993 | Nakao et al. |
| 5,190,555 A | 3/1993 | Wetter et al. |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,312,416 A | 5/1994 | Spaeth et al. |
| 5,341,815 A | 8/1994 | Cofone et al. |
| 5,352,184 A | 10/1994 | Goldberg et al. |
| 5,354,303 A | 10/1994 | Spaeth et al. |
| 5,465,731 A | 11/1995 | Bell et al. |
| 5,480,404 A | 1/1996 | Kammerer et al. |
| 5,486,183 A | 1/1996 | Middleman et al. |
| RE35,164 E | 3/1996 | Kindberg et al. |
| 5,899,694 A | 5/1999 | Summer |
| 6,402,722 B1 | 6/2002 | Snow et al. |
| 2006/0058776 A1 | 3/2006 | Bilsbury |
| 2011/0087235 A1 | 4/2011 | Taylor et al. |

FOREIGN PATENT DOCUMENTS

| | | |
|---|---|---|
| DE | 3542667 | 6/1986 |
| DE | 19624826 | 1/1998 |
| FR | 1272412 | 8/1961 |
| WO | WO 2011/044562 A1 | 4/2011 |

MINIMALLY INVASIVE REMOVAL DEVICE WITH BREAKAWAY SHEATH

CROSS REFERENCE TO RELATED APPLICATIONS

The present application is a continuation application of U.S. Ser. No. 10/508,445, filed Sep. 16, 2004, now U.S. Pat. No. 8,016,771 which claims the benefit of and priority to International Application Serial No. PCT/US03/09133, filed Mar. 21, 2003, which, in turn, claims the benefit of and priority to U.S. Provisional Application Ser. No. 60/368,191, filed on Mar. 27, 2002, the entire contents of which were incorporated herein by reference.

BACKGROUND

1. Technical Field

The present disclosure relates to devices used for facilitating the removal of tissue portions during surgical procedures and, more particularly, to devices for removing tissue portions during minimally invasive surgical procedures. The present disclosure further relates to methods of collapsing the devices disclosed herein in order to reduce the cross-sectional profile thereof.

2. Background of Related Art

As a result of technological improvements in surgical instruments, surgical procedures using minimally invasive techniques can be performed causing less trauma to the patient. It is desirable to use smaller incisions so that a trocar or a cannula inserted into the incision is desirably smaller. Minimally invasive surgical procedures, however, have their limitations as the use of smaller diameter trocars require increasingly innovative and novel solutions for many traditional instrument applications such as tissue removal instruments. Tissue removal instruments have tissue removal bags carried on deformable or inflatable frames which also define the opening of the bag. The inflatable frame instruments have openings that require an additional system for pressurization of the frame and/or bag which may also be a separately inflated member. Inflatable tissue removal instruments are vulnerable to accidental perforations and/or deflation, and are dependent upon the rigidity of the inflatable structure to support and contain the tissue as it is loaded into the bag and withdrawn through the trocar. It is desirable to decrease the cross-sectional area of the instrument for use with reduced diameter trocar systems.

A continuing need exists for an improved tissue removal system having a reduced cross-sectional diameter for passage through reduced diameter cannulas of trocar systems.

SUMMARY

According to one aspect of the present disclosure, a tissue removal device includes an elongate shaft having a distal end and a proximal end, wherein the elongate shaft defines a longitudinal axis, a bag support defining an opening, the bag support being collapsible and expandable to open and close the opening, a bag operatively attached to the bag support, the bag having an open first end operatively secured to the bag support and a closed end, the first end being connected to the support so that when the bag support is in the collapsed position the bag opening is substantially closed. The bag has folds including at least one transverse fold. It is contemplated that the tissue removal device further includes a tube for receiving the shaft, bag support and bag.

It is envisioned that the folds include folds approximately parallel with the longitudinal axis. It is further envisioned that a sheath is disposed about the bag assembly. Preferably, the sheath includes a weakness for breaking away from the bag. The sheath can be fabricated from a flexible heat shrinking polymer. It is contemplated that the sheath is in the form of a mesh, a net and/or a lattice.

The tissue removal device further includes an actuation system operatively connected to the sheath in order to facilitate removal of the sheath from the bag assembly. It is envisioned that the actuation system includes a tear line formed in the sheath to facilitate tearing of the sheath. It is further envisioned that the actuation system includes a cord operatively connected to the tear line for facilitating the tearing of the sheath along the tear line. It is contemplated that the cord is connected to a control portion at the proximal end of the shaft.

It is envisioned that the actuation system includes an expandable member positioned within the bag assembly. Expansion of the expandable member is preferably initiated remotely from the bag.

It is further envisioned that the bag has a proximal edge and a distal edge and includes a slot formed in the vicinity of the bag support near the proximal edge to enable the diameter of the bag to be adjusted. In addition, the bag includes a control line for drawing the slot closed.

The bag can have any shape, including at least one of a conical and a trapezoidal shape. It is further contemplated that the tissue removal device includes a control portion operatively coupled to the proximal end of the shaft.

According to another aspect of the present disclosure, a method of collapsing a bag of a tissue removal device is disclosed. The method includes the steps of providing a minimally invasive tissue removal device including a shaft having a distal end and a proximal end and defining a longitudinal axis, a bag support, and a bag attached to the bag support, the bag having an upper end operatively coupled to the bag support and a lower end. The method further includes the step of folding the bag transversely with respect to the longitudinal axis. It is envisioned that the bag is folded onto itself such that the proximal edge crosses the distal edge.

The method further includes the step of at least one of folding the bag so that the folds are approximately parallel to the longitudinal axis. It is envisioned that the bag support has a collapsed position and an expanded position and further includes collapsing the upper end of the bag using the support. It is further envisioned that the bag is folded onto its self such that the proximal edge of the bag is substantially parallel with the longitudinal axis and/or such that the proximal terminal edge of the bag is substantially aligned with the longitudinal axis. It is contemplated that the bag is folded so that a portion of the bag is disposed distally of a distal end of the support.

The method further includes the step of placing the folded bag and bag structure into a sheath. It is envisioned that the sheath includes a weakness and further includes the step of tearing the sheath at the weakness so as to release the bag.

According to a further aspect of the present disclosure, there is provided a minimally invasive tissue removal device for passage through a cannula, the device including an elongate shaft having a distal end portion and a proximal end portion, the elongate shaft defining a longitudinal axis, and a bag assembly operatively coupled to the distal end portion of the shaft. The bag assembly includes a bag support structure having a first position and a second position, and a bag having an upper end and a lower end, the upper end having an open position and a closed position and being operatively secured to the bag support such that when the bag support is in the first position, the upper end of the bag is substantially open and when the bag support is in the second position, the upper end of the bag is substantially closed, the bag being folded over onto itself so as to form a transverse fold.

The tissue removal device further includes a removable sheath disposed about the bag assembly when in the bag is in the folded condition. It is envisioned that the bag has a proximal edge and a distal edge and wherein the bag is folded such that the proximal edge is substantially aligned with the longitudinal axis.

According to yet another aspect of the present disclosure, there is provided a minimally invasive tissue removal device for passage through a trocar, the device including an elongate shaft having a distal end portion and a proximal end portion, the elongate shaft defiling a longitudinal axis, a bag support at the distal end of the shaft having a first position and a second position, the bag defining a plane when in the first position, and a bag having an open end and a closed end opposite the open end, the bag extending along a bag axis which is perpendicular to the longitudinal axis, the bag having an open position and a closed position, wherein the bag is folded over onto itself such that the bag axis is oriented substantially parallel to the longitudinal axis of the shaft.

It is envisioned that the bag is folded over onto itself, into a cylinder adjacent the bag support.

The presently disclosed endoscopic tissue removal device with breakaway sheath, together with attendant advantages, will be best understood by reference to the following detailed description in conjunction with the figures below.

BRIEF DESCRIPTION OF THE DRAWINGS

By way of example only, preferred embodiments of the present disclosure will be described herein with reference to the accompanying drawings, in which.

DETAILED DESCRIPTION OF PREFERRED EMBODIMENTS

Figure 1:
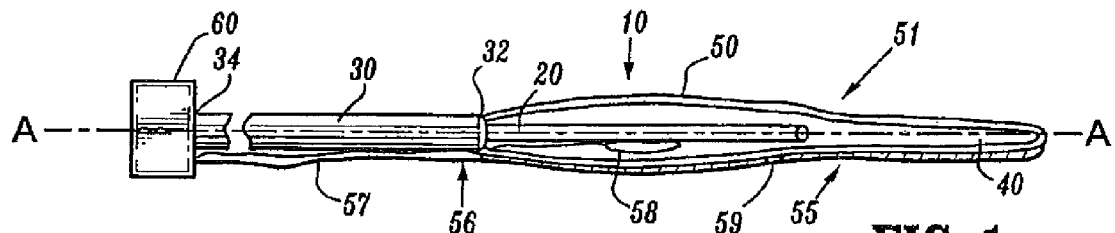
FIG. 1 is a cross-sectional view of a tissue removal device with a breakaway sheath in a folded position, in accordance with an embodiment of the present disclosure.

Preferred embodiments of the presently disclosed endoscopic tissue removal device will now be described in detail with reference to the drawing figures wherein like reference numerals identify similar or identical elements. In the drawings and in the description which follows, the term "proximal", as is traditional will refer to the end of the device which is closest to the operator, while the term "distal" will refer to the end of the device which is furthest from the operator.

Referring initially to FIGS. 1-4, one preferred embodiment of a tissue removal device in accordance with the present disclosure, is shown generally as 10. Device 10 includes a bag assembly 15, a shaft 30, a control system 60 and desirably includes a breakaway sheath 50. Shaft 30 defines a longitudinal axis "A". Bag assembly 15 includes a bag support structure or bag support 20 and a bag 40 operatively attached to bag support 20.

Figure 2:
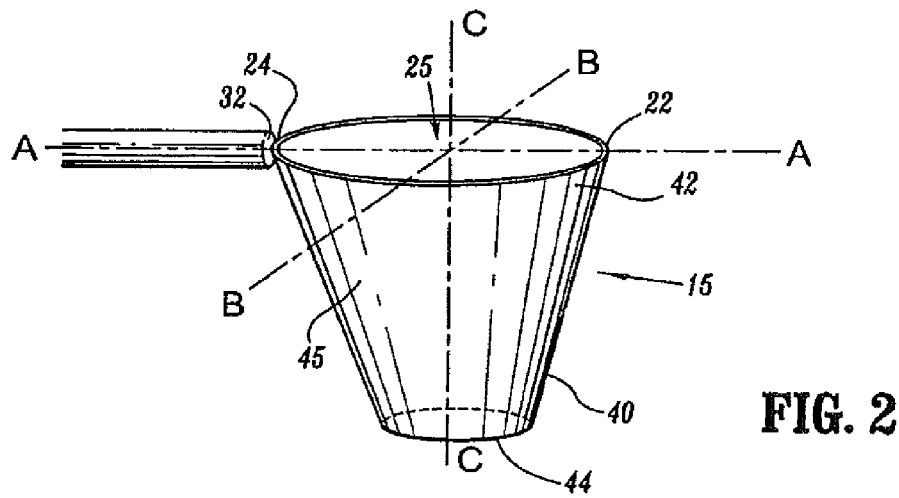
FIG. 2 is a top perspective view of the tissue removal device in accordance with the embodiment of FIG. 1 in an unfolded position.
Figure 3:
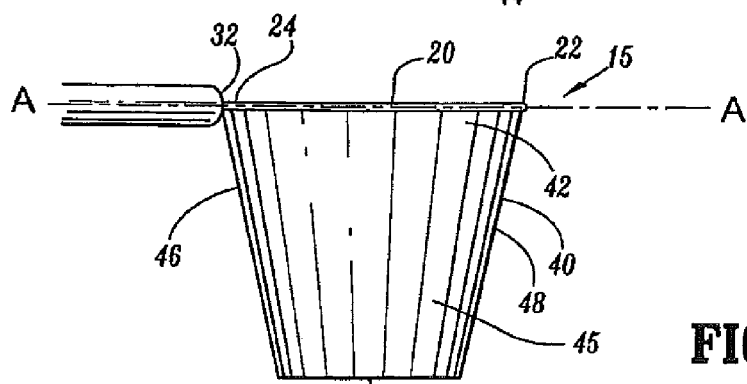
FIG. 3 is a side elevational view of the tissue removal device of FIG. 1, in a method in accordance with a further embodiment.
Figure 4:
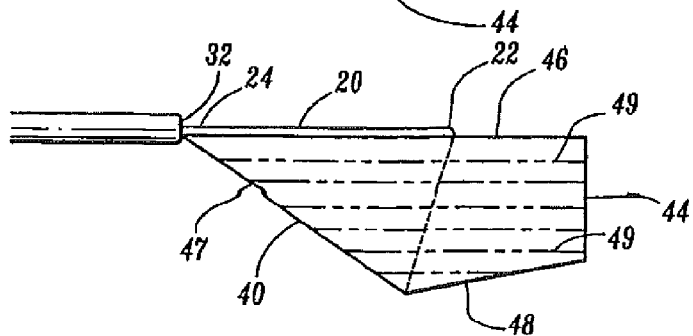
FIG. 4 is a side elevational view of the tissue removal device of FIG. 3, at a later stage in the method.

As seen in FIGS. 2-4, bag support 20 has a distal end portion 22 and a proximal end portion 24. Bag support 20 is deformable and is preferably biased to an open ring shape. The bag support 20 may comprise any openable structure. Bag support 20 may comprise one or more flexible resilient strips of metal or any other flexible and/or resilient materials. Bag support 20 is positioned within a plane A-B defined by axis "A" and a perpendicular axis "B". An axis "C" intersects and is perpendicular to axes "A and B". Bag support 20 is biased to the open position and is compressible to an elongate configuration wherein the dimension of the ring along minor axis "C" can approach zero, the sides of bag support 20 are close or in direct contact with one another. The specific geometric shape and size of bag support 20 or bag assembly 15 is dependent, however, upon the specific application of device 10. Thus, bag support 20 when in the open position can define any shape, such as a two dimensional geometric opening in the form of an ellipse, a triangle, or an oval, as well as three dimensional openings such as a scoop, for example.

Pouch or bag 40 is connected to bag support 20 and has a wall 45 defining a truncated conical shape. The bag may be connected to the bag support by a variety of known means such as the upper end of the bag being configured to receive the bag support. The bag 40 includes a flexible film or sheet and may be formed from a substantially transparent polymeric material. Polyurethane, latex or any other biocompatible material may be used. The bag may have any dimensions suitable for entrapping and/or removing tissue. A first end 42 of bag 40 defines opening 25 and a second end 44 provides a secured or closed end having sufficient strength to retain the tissue portions during the withdrawal of bag assembly 15 through reduced diameter trocars. Bag assembly 15 is desirably suitably configured for use in positioning, isolating, retaining and removing tissue portions during minimally invasive surgery.

Device 10 has a first position wherein bag assembly 15 is open such that bag 40 is unfolded and bag support 20 is uncompressed and defines an opening 25 for receiving tissue portions. In a second position, bag assembly 15 closed so that support 20 is compressed and bag 40 is tightly folded, rolled, and/or compressed. The use of the terms or phrase: folding of bag assembly 15, is intended to encompass at least the terms such as those identified above that are employed in the general process of folding bag 40 and may include collapsing the bag support 20. Folded bag assembly 15 becomes a sheathed bag assembly 51 in the second position when packaged in breakaway sheath 50. Sheathed bag assembly 51 has a reduced cross-sectional area perpendicular to the longitudinal axis or diameter for passing through a reduced diameter trocar. Reduced diameter trocars include trocars having inside diameters as small as 12 millimeters, and smaller. It is also envisioned that the present disclosure can attain additional reductions in the outside diameters of sheathed bag assembly 51. Preferably, when bag 40 is in the first position, bag 40 generally extends in the direction of axis "C".

Shaft or pusher 30 has a distal end portion 32 and a proximal end portion 34. Bag assembly 15 is operatively connected with distal end portion 32, such as, by connecting bag support 20 to distal end portion 32 of shaft 30. The shaft 30 is desirably formed from a polymeric material, but may be formed from any medical grade material. The shaft is slidably received in a tube, as discussed in U.S. Pat. Nos. 5,647,372 and 5,465,731, the disclosures of which are entirely incorporated by reference herein. Control portion 60 (symbolically shown) is connected to proximal end portion 34 for positioning, manipulating and orienting bag support 20 and bag 40 during surgery. Initially, bag assembly 15 is disposed within the tube and bag 40 is disposed on bag support 20 and contained in a sheath 50. Shaft 30 is used to position sheathed bag assembly 51 through the reduced diameter trocar and manipulate bag assembly 15 to the first or open position during minimally invasive surgery. The structure of shaft 30, operational deployment of bag assembly 15 and associated structure are described in commonly owned U.S. Pat. No. 5,647,372 entitled "Specimen Retrieval Pouch and Method of Use" and U.S. Pat. No. 5,465,731 entitled "Specimen Retrieval Pouch and Method of Use," both of which are incorporated entirely herein by reference. When shaft 30 is advanced through the tube using control portion 60, the control portion 60 is manipulated so that bag support 20 exits the tube. Shaft 30 can have a distal end 32 portion configured to bend or have a hinged connection, far example, which is manipulatable from control portion 60 and facilitates orientation of bag 30 after bag assembly 15 has been introduced into the body for receiving tissue portions and any other specimens therein.

Breakaway sheath 50 is configured and adapted to package and retain bag assembly 15 in the second closed position having a reduced dimension along the "C" axis. Preferably, breakaway sheath 50 is configured to breakaway or break apart from bag assembly 15. Breakaway sheath 50 preferably includes an easily manipulated release mechanism 55, in control portion 60, such that bag assembly 15, including bag 40 and bag support 20, can be easily released from sheath 50 by control portion 60. Once sheath 50 is broken away, the bias of bag support 20 and/or bag 40 causes bag assembly 15 to expand to the first position.

In one preferred embodiment, breakaway sheath 50 includes a flexible layer 52, which may include a medical grade plastic, such as for example, a single layer of film, or a single or a multilayer laminate. Layer 52 includes a weakness or perforations. Layer 52 has suitable structural integrity for retaining bag 40 and bag support 20 in the folded and/or compressed position against any bias inherent in bag assembly 15 toward the second position. Layer 52 can have a uniform thickness, be continuous or discontinuous, provide a hermetic seal, or include reinforced portions in a geometric pattern, for example. Layer 52 could comprise a sheet, mesh, net, lattice or a combination thereof.

Layer 52 is wrapped around the folded bag 40 so that the folded bag 40 is disposed on bag support 20. Layer 52 is preferably configured as a shrink wrapped envelope, tube, or other layer shrunk and/or compressed around bag assembly 15 when folded in the second closed position. Layer 52 preferably closely conforms to and/or is tightly positioned around bag assembly 15. Sheath 50 can be fabricated from a suitable range of materials such that sheathed bag assembly 51 can be a flexible or rigid structure. Thus, it is envisioned that sheathed bag assembly 51 can be sufficiently flexible so as to be flexed into an arcuate shape from control portion 60.

In another alternative embodiment, breakaway sheath 50 can be a rigid or semi-rigid housing with or without perforations. This configuration can be employed to mechanically compress and secure bag assembly 15 in a fixed position. The housing can also be readily adaptable to vacuum packing. In operation, the housing could be easily opened using a remotely operated release mechanism 55 operated from control portion 60 to disconnect a pin or lever mechanism, for example. The housing can be withdrawn separately through the reduced diameter trocar after releasing bag assembly 15.

Alternatively, breakaway sheath 50 may be connected to bag assembly 15 such that when sheathed bag assembly 51 is released, sheath 50 remains at least partially connected to bag assembly 15. In this configuration, sheath 50 could be a series of bands or an extended flap connected to bag assembly 15, for example, such that bag assembly 15 can be secured in the second closed position using the integral bag/sheath combination and could be held in the second closed position by an adjustable mechanical fastening device as well as by being shrink wrapped. Alternatively, sheath 50 can be connected to bag 40 by a cord or a ribbon (not shown). The cord would allow sheath 50 to be withdrawn with, but sequentially after, bag assembly 15, with tissue portions positioned therein, when sheath 50 is withdrawn through the reduced diameter trocar.

Breakaway sheath 50 may be fabricated from any suitable medical grade plastic or composite type material having the requisite strength and resistance to stretching. Preferably, the material is heat shrinkable. Alternate embodiments having rigid or semi-rigid enclosures as well as integral bag 40/sheath 50 systems may be fabricated from one or more suitable medical grade plastics, composites, or metals.

Release mechanism 55 is activated from control portion 60 by a surgeon. Release mechanism 55 preferably includes the weakness, or perforation, which may comprise an easily openable tear line 59 in layer 52 and an actuation system 56. Tear line 59 can be formed by one or more score lines, perforation lines, or edges that are continuous, but can be discontinuous. Actuation system 56 has components such as a suture, wire, pull tab, or cord 57 configured for connecting control portion 60 to tear line 59 and for facilitating the tearing of tear line 59 and the release of sheath 50. For example, a first end of cord 57 is connected to a distal end of sheath 50 and a second end of cord 57 is disposed at control portion 60 so that sheath 50 can be released by the drawing of one or more sutures 57 in a proximal direction to rupture sheath 50 along tear line 59 and release bag assembly 15. Any other mechanism for releasing sheath 50 may be used.

Actuation system 56 could also be at least partially positioned as a connecting mechanism for mating edges of sheath 50. For example, cord 57 positioned on opposing edges of sheath 50 could also be a connecting mechanism linking portions of sheath 50 together in the second closed position. Cord 57 acting as the connecting mechanism could be released by a cutting or severing device configured to be pulled proximally against and severing cord 57 thereby releasing sheathed bag assembly 51. In the alternative, release mechanism 55 could be an integral part of layer 52, such as an elongated pull tab or cord 57, connected to a breakaway mechanical seam such as a zipper or similar mechanical snap or pressure seal configured for opening upon separation or drawing of the tab through the seam.

A further alternative remote actuation system 56 could include, for example, an expandable portion 58 strategically positioned within bag assembly 15 that could be expanded from control portion 60 to rupture tear line 59 of sheath 50. Expandable portion 58 could be a mechanical device such as a biasing member. Expandable portion 58 may comprise an expandable bladder in communication with an external source of fluid via control portion 60.

Breakaway sheath 50 can also be configured for an incremental release that allows the gradual expansion of sheathed bag assembly 51 from the second closed position to the first open position. For example, release mechanism 55 can include multiple sutures 57 connected with one or more tear lines 59 configured to accommodate a gradual and controlled expansion of bag assembly 15.

Referring now to FIGS. 3 and 4, a method of folding bag assembly 15 in accordance with an embodiment is depicted. Embodiments of the invention are particularly advantageous for a reduced diameter device for introduction during minimally invasive surgical procedures. Bag assembly 15 is positioned from the first open or unfolded position (as seen in FIG. 3) to the second closed or folded position (as seen in FIG. 1) by compressing bag support 20 such that it forms a narrow shape with opposed bends at the proximal end portion 24 and distal end portion 22. The sides of bag support 20 can be in direct contact with or in close proximity to, one another. The compressing of bag support 20 also compresses bag 40 into a flattened shape having a proximal folded edge 46 and a distal folded edge 48 such that opposing portions of wall 45 are in close to or in direct contact with one another. Bag 40 also extends away from bag support 20 to a bottom or second end 44. Bottom end 44 extends in a direction approximately parallel with axis "A".

Bottom or second end 44 of bag 40 is bent or folded over on itself such that proximal folded edge 46 is approximately aligned and in apposition with bag support 20 and bottom end 44 is disposed so that bottom end 44 extends in a direction parallel with axis "C", as best seen in FIG. 4. This folding step also forms a transverse fold 47 running at an angle relative to longitudinal axis "A". In certain embodiments, fold 47 is preferably approximately 45 degrees relative to longitudinal axis "A". Transverse fold 47 extends from edge 46 to edge 48. Preferably, transverse fold 47 begins at the junction of the proximal folded edge 46 with proximal end portion 24 and extends across bag 40 to distal folded edge 48. Bag 40 is then folded or rolled upward to be disposed parallel to longitudinal axis "A". Bag 40 may be folded along fold lines 49, for example, or the bag may be rolled, without creating any fold lines. This forms the final folded or second position of bag assembly 15 which is prepared for packaging with breakaway sheath 50, as described above. The folding of bag 40 in this manner has been found to produce a low profile folded bag, such that smaller diameter tubes can be used.

This folding or rolling process advantageously extends bag 40 along longitudinal axis "A" prior to the final folding step such that the folding of the material of bag 40 is extended over a greater distance along longitudinal axis "A". This enables bag 40 to be more tightly folded and/or rolled into a smaller diameter for packaging and passing through reduced diameter trocars. In certain embodiments, the above process is capable of folding and sheathing bag assembly 15 into a configuration having an outside diameter sized for use with a trocar with an internal diameter of approximately 12 millimeters, or smaller.

It is readily envisioned that further reductions in diameter can be made to bag assembly 15. For example, the steps of the folding or rolling process can be augmented by aspirating bag 40 sufficiently or folding bag 40 in a vacuum to avoid entrapping air in bag 40 during the folding process. Furthermore, bag 40 may be folded over on itself more than once before bag 40 is folded or rolled upwardly toward bag support 20.

It is also envisioned that the shrink wrap process of sheath 50 can further compress or reduce the diameter of bag assembly 15. The shrink wrap process can also be configured to proceed sequentially along the longitudinal-axis "A", any other suitable directional orientation, or combination of directions of bag assembly 15, for example, to advantageously force air from folded bag 40 to further reduce the volume of bag 40 before sheathing. In an alternative embodiment, bag 40 is vacuum packed or folded in a vacuum and shrink wrapped/sealed using flexible plastic layer 52.

Figure 5:
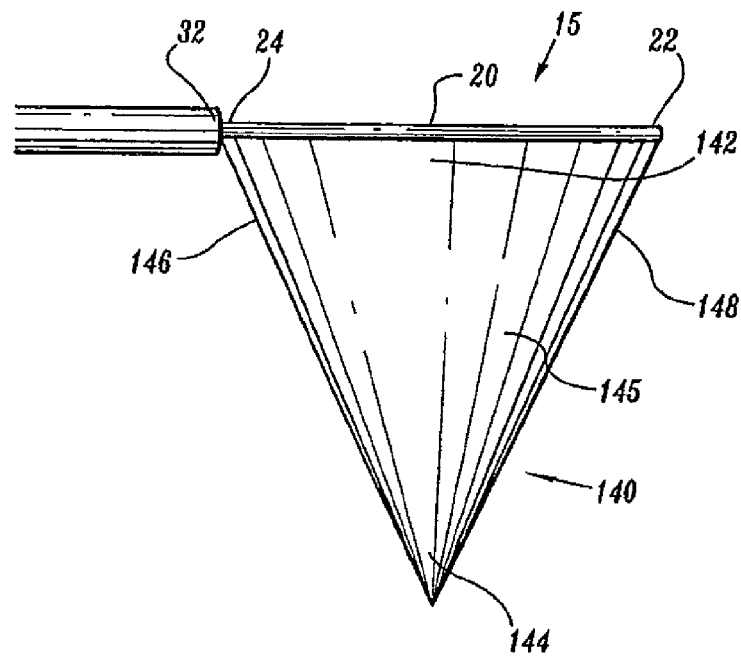
FIG. 5 is a side elevational view of a tissue removal device in accordance with a further embodiment of the present disclosure.
Figure 6:
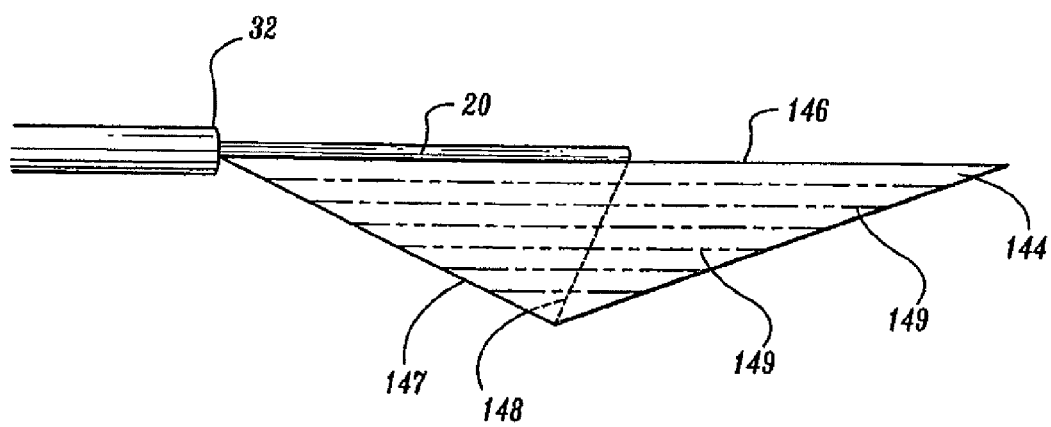
FIG. 6 is a side elevational view of the tissue removal device in a method in accordance with a further embodiment.
Figure 7:
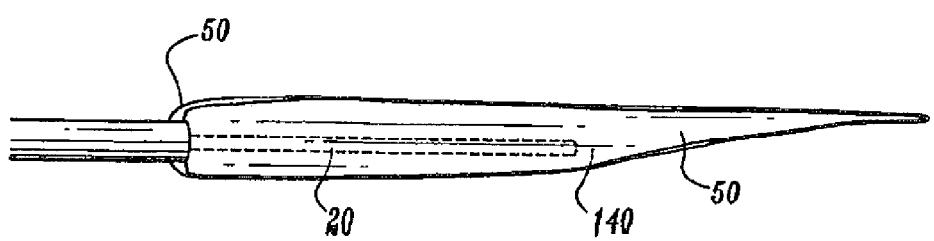
FIG. 7 is a side elevational view of the tissue removal device of FIG. 6 at a later stage in the method.

The bag may have a wide variety of shapes. Referring now to FIGS. 5-7, reductions in the diameter of a folded bag assembly 15 can be achieved in another embodiment including a bag 140 having a conical shape. Bag 140 includes a wall 145 having a first end 142 and a second end 144. First end 142 defines an opening (not shown) while second end 144 defines a tip that is a closed end. End 144 points downwardly along axis "C".

A method of packaging or folding bag 140 in a configuration having a low profile, reduced diameter, or small dimension along axis "C", is also described herein. Bag 140 is positioned from the first open or unfolded position (as seen in FIG. 5) to the second closed or folded position (as seen in FIG. 7) by compressing bag support 20 such that it forms a narrow shape with opposed proximally and distally positioned bends forming two arcuate sides at distal end 22 and proximal end 24, positioning the sides in contact or in close proximity to one another. The compressing of bag support 20 also compresses bag 140 into a flat triangular shape having a proximal folded edge 146 at the proximal end of bag 140 and a distal folded edge 148 at the distal end of the bag 140 such that opposing portions of wall 145 are close or in direct contact. Second end 144 of bag 140 extends away from bag support 20.

Bottom or second end 144 of bag 140 is repositioned or folded on top of itself such that proximal folded edge 146 is approximately aligned with or approximately parallel to bag support 20 and so that bottom end 44 is directed along axis "A". Depending upon the dimensions of the bag, bag 140, in the second position, includes second end 144 extending in a distal direction and positioned at least partially distal to edge 148, as shown in FIG. 6. This step also forms a transverse fold 147 starting at end 146 toward end 148, or preferably at the junction of the proximal end 146 with proximal end portion 24 and extending across bag 140 to the distal folded edge 148. Bag 140 is then folded or rolled upward to be disposed parallel to longitudinal axis "A" and may be folded along fold lines 149, for example. This forms the final folded reduced diameter position of bag assembly 15 prior to packaging of bag assembly 15 with breakaway sheath 50.

Figure 8:
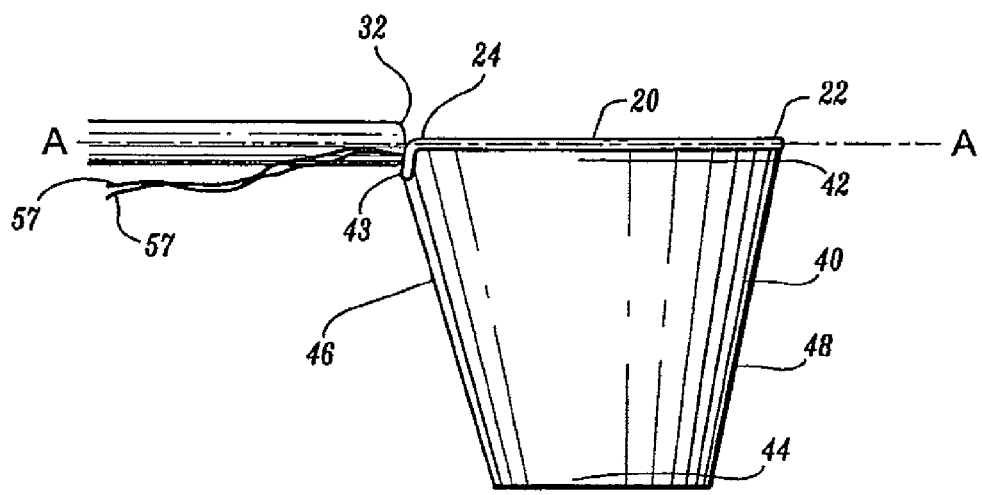
FIG. 8 is a side elevational view of a tissue removal device in accordance with another embodiment of the present disclosure.
Figure 9:
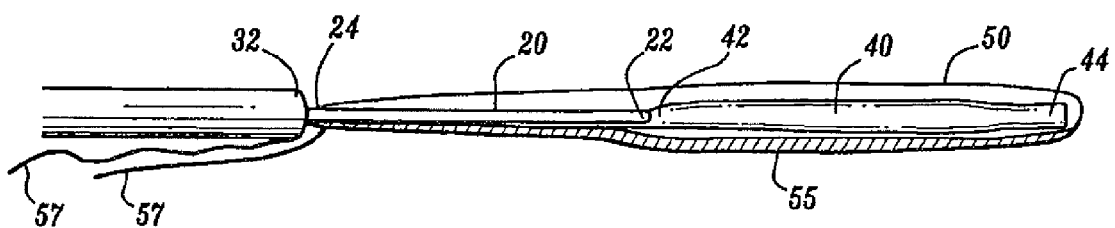
FIG. 9 is a side view of a tissue removal device in accordance with the embodiment of FIG. 8 in a folded position.

As shown in FIGS. 8 and 9, reductions in the diameter of bag assembly 15 in the second position can also be achieved by configuring bag 40 to be at least partially separable from bag supports 20, in the vicinity of bag support 20. Bag 40 is configured with a rim 21 that receives bag support 20. In the first position, the first end 42 of the bag is able to slide along bag support 20 in the at least partially folded position. First end 42 is desirably fixedly connected to bag support 20 at distal end 22 using an adhesive, for example. Bag 40 in this configuration can be suspended over bag support 20 or at least partially suspended from bag support 20. In this configuration, bag 40 retains its generally conical shape including second end 44, but has a break or slot 43 in the vicinity of proximal folded edge 46 in the vicinity of proximal end portion 24 configured to enable bag 40 to adjust its diameter and slide around bag support 20 from proximal end 24 to distal end 22. The slot 43 is sized to enable bag 40 to receive bag support 20 when the bag support is in either the collapsed or expanded positions. Thus, first end 42 of bag 40 in the vicinity of fold 46 can at least partially separate and slide freely along the sides of bag support 20 for folding into the second position. This advantageously accommodates first end 42 being slid at least partially towards distal end 22 folding bag 40 into a low profile configuration. The second end 44 desirably extends distally from distal end 22 generally along longitudinal axis "A", to facilitate folding into a low profile configuration. Bag 40 can then be rolled or folded with minimal overlap with bag support 20.

After being passed through the trocar during minimally invasive surgery, first end 42 of bag 40 can be slid along bag support 20 toward proximal end 24, concurrent with or prior to the expansion of bag support 20, by a cord 57. The cord is desirably deployed at control portion 60. In the alternative, bag 40 could be biased to slide toward distal end 22 concurrent with the expansion of bag support 20 to the first position. The slot 43 is desirably closed after bag assembly 20 has expanded by further drawing control lines 57 proximally such that the sides of slot 43 are brought together and slot 43 is closed. In further embodiments, the bag opening 25 may be closed using cord 57 or a separate suture, cord or line.

Although the illustrative embodiments of the present disclosure have been described herein, it is to be understood that the disclosure is not limited to those precise embodiments, and that various other changes and modifications may be affected therein by one skilled in the art without departing from the scope or spirit of the disclosure. For example, in further embodiments, a collapsible or flexible container other than a bag may be used. All such changes and modifications are intended to be included within the scope of the disclosure.

What is claimed:

1. A tissue removal device, comprising:
   an elongate member having a distal end and a proximal end with a longitudinal axis defined therebetween, the elongate member defining a bag storage cavity therein with an opening at the distal end;
   a shaft including a control portion and being movable coaxially within the elongate member via the control portion from a retracted position to an advanced position;
   an expandable bag support operatively attached to the shaft and configured and dimensioned to be positioned completely within the elongate member when the shaft is in the retracted position and to move into an expanded position when the shaft is in the advanced position; and
   a bag operatively supported by the expandable bag support, the bag defining an opening adjacent the expandable bag support and tapering to a closed end, said bag being rolled onto itself and being disposed completely within the bag storage cavity of the elongate member when the shaft is in the retracted position, such that at least the closed end of the bag extends distally beyond the expandable bag support.

2. The tissue removal device of claim 1, further comprising a tube for receiving the shaft, the bag support and the bag.

3. The tissue removal device of claim 1, wherein the bag is rolled in a direction transverse to the longitudinal axis.

4. The tissue removal device of claim 3, wherein the bag is rolled in a direction substantially orthogonal to the longitudinal axis.

5. The tissue removal device of claim 1, further including a sheath disposed about the bag.

6. The tissue removal device of claim 5, wherein the sheath includes a weakness for breaking away from the bag.

7. A tissue removal device, comprising:
   an elongate shaft having a distal end and a proximal end, wherein the elongate shaft defines a longitudinal axis; and
   a bag operatively attached to a bag support movable through the elongate shaft between advanced and retracted positions, the bag support having proximal and distal ends, and being further movable between:
   (i) a first, unfolded position, wherein the bag extends downwardly from the bag support;
   (ii) a second, folded position, wherein the bag defines an edge extending distally from the proximal end of the bag along an axis transverse in relation to the longitudinal axis to a distal portion positioned distally beyond the bag support; and
   (iii) a third, rolled position, wherein the bag is rolled onto itself, the bag having an open first end operatively secured to the bag support, and a closed end, the first end being connected to the support so that when the bag support is in a collapsed position the bag opening is substantially closed.

8. The tissue removal device of claim 7, wherein the edge extending distally from the proximal end of the bag is substantially linear.

9. The tissue removal device of claim 7, wherein the transverse axis is oblique with respect to the longitudinal axis.

10. The tissue removal device of claim 7, further comprising a tube for receiving the shaft, the bag support and the bag.

11. The tissue removal device of claim 7, wherein the bag is rolled in a direction transverse to the longitudinal axis.

12. The tissue removal device of claim 11, wherein the bag is rolled in a direction substantially orthogonal to the longitudinal axis.

13. The tissue removal device of claim 7, further including a sheath disposed about the bag.

14. The tissue removal device of claim 13, wherein the sheath includes a weakness for breaking away from the bag.

15. A method of collapsing a bag secured to a bag support structure of a tissue removal device, the method comprising:
   moving the bag from a first, unfolded position, wherein the bag extends downwardly from the bag support, to a second, folded position, wherein the bag defines an edge extending distally from a proximal end of the bag along an axis transverse in relation to a longitudinal axis of the tissue removal device to a distal portion positioned distally beyond the bag support structure, to a third, rolled position, wherein the bag is rolled onto itself.

16. The method according to claim 15, wherein moving the bag from the first position to the second position includes folding the bag such that the transverse axis along which the edge extends is oblique with respect to the longitudinal axis.

17. The method according to claim 15, wherein moving the bag from the second position to the third position includes rolling the bag, onto itself, in a direction transverse in relation to the longitudinal axis.

18. The method according to claim 17, wherein moving the bag from the second position to the third position includes rolling the bag, onto itself, in a direction substantially orthogonal in relation to the longitudinal axis.

* * * * *